United States Patent [19]

Sandberg

[11] Patent Number: 5,726,753
[45] Date of Patent: Mar. 10, 1998

[54] INTRACAVITY PARTICLE DETECTION USING OPTICALLY PUMPED LASER MEDIA

[75] Inventor: Jon C. Sandberg, Boulder, Colo.

[73] Assignee: Research Electro-Optics, Inc., Boulder, Colo.

[21] Appl. No.: 607,289

[22] Filed: Feb. 26, 1996

[51] Int. Cl.⁶ ................................................. G01N 21/00
[52] U.S. Cl. ...................... 356/338; 356/339; 356/337
[58] Field of Search ............................. 356/338, 339, 356/335, 336, 388, 332, 436, 440, 246, 438, 419, 427; 372/21, 22, 29, 34, 39, 32, 41, 70, 76, 97, 26; 331/94.5; 378/4, 20, 22; 250/222.2

[56] References Cited

U.S. PATENT DOCUMENTS

| | | | |
|---|---|---|---|
| Re. 34,729 | 9/1994 | Sipes, Jr. ...................... | 372/75 |
| 3,753,145 | 8/1973 | Chesler ......................... | 331/94.5 |
| 4,571,079 | 2/1986 | Knollenberg .................. | 356/336 |
| 4,594,715 | 6/1986 | Knollenberg .................. | 372/32 |
| 4,653,056 | 3/1987 | Baer et al. ..................... | 372/27 |
| 4,665,529 | 5/1987 | Baer et al. ..................... | 372/107 |
| 4,685,802 | 8/1987 | Saito et al. .................... | 356/339 |
| 4,723,257 | 2/1988 | Baer et al. ..................... | 372/108 |
| 4,739,507 | 4/1988 | Byer et al. ..................... | 372/22 |
| 4,746,215 | 5/1988 | Gross ............................ | 356/339 |
| 4,798,465 | 1/1989 | Knollenberg .................. | 356/336 |
| 4,809,291 | 2/1989 | Byer et al. ..................... | 372/75 |
| 4,872,177 | 10/1989 | Baer et al. .................... | 372/75 |
| 5,033,851 | 7/1991 | Sommer ........................ | 356/338 |
| 5,092,675 | 3/1992 | Sommer ........................ | 356/338 |
| 5,285,467 | 2/1994 | Scheps .......................... | 372/69 |

OTHER PUBLICATIONS

R.G. Knollenberg, "Measurement of Particle sizes Below 0.1 Micrometers", Journal of Environmental Sciences, Jan.-Feb. 1985.

Zhou et al., "Efficient, Frequency-Stable laser--diode-pumped Nd:YAG laser", Optics Letters, vol. 10, No. 2, pp. 62–64, Feb. 1985.

Primary Examiner—Frank G. Font
Assistant Examiner—Michael P. Stafira
Attorney, Agent, or Firm—Robert E. Harris

[57] ABSTRACT

Interacvity particle detection is disclosed using optically pumped laser media. A laser medium, positioned within a laser cavity, is end-pumped by an optical pump source to excite the laser medium to provide laser light within the laser cavity, and a detecting region, also positioned within the laser cavity and capable of having particles, or particle-containing fluid, therein, is exposed to the laser light whereby light is effected, as by being scattered, by particles in the detecting region with the scattered light being indicative of particles, such as small particles having a size of between 0.05 and 10 microns, causing the light to be scattered so that the scattered light, when collected, can be used to provide an output indicative of particles at the detecting region. A laser cavity, having therein a solid state laser medium end-pumped by a semiconductor laser providing focused light into the laser medium to achieve gain-aperturing, provides high intracavity power, such as about 550 Watts, to enable detection within the laser cavity of small particles, including particles in a fluid, such as air, passing through the detecting region at high flow rates, including flow rates at, or greater than, one cubic foot per minute.

36 Claims, 7 Drawing Sheets

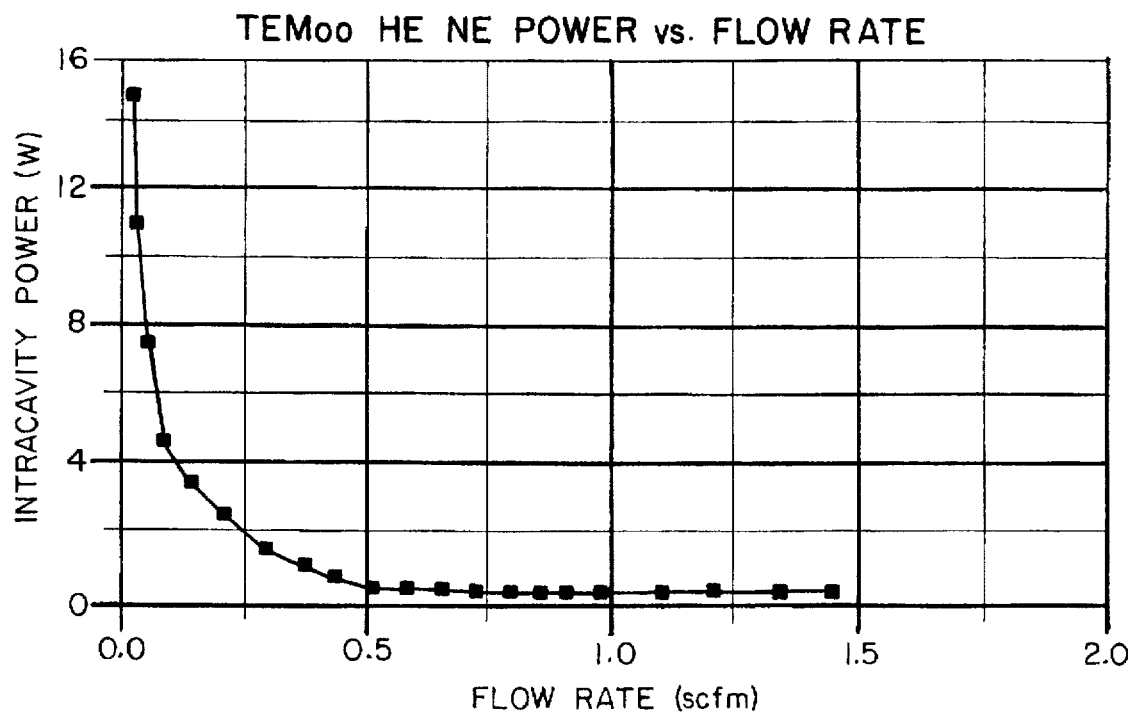
*Fig_2A*
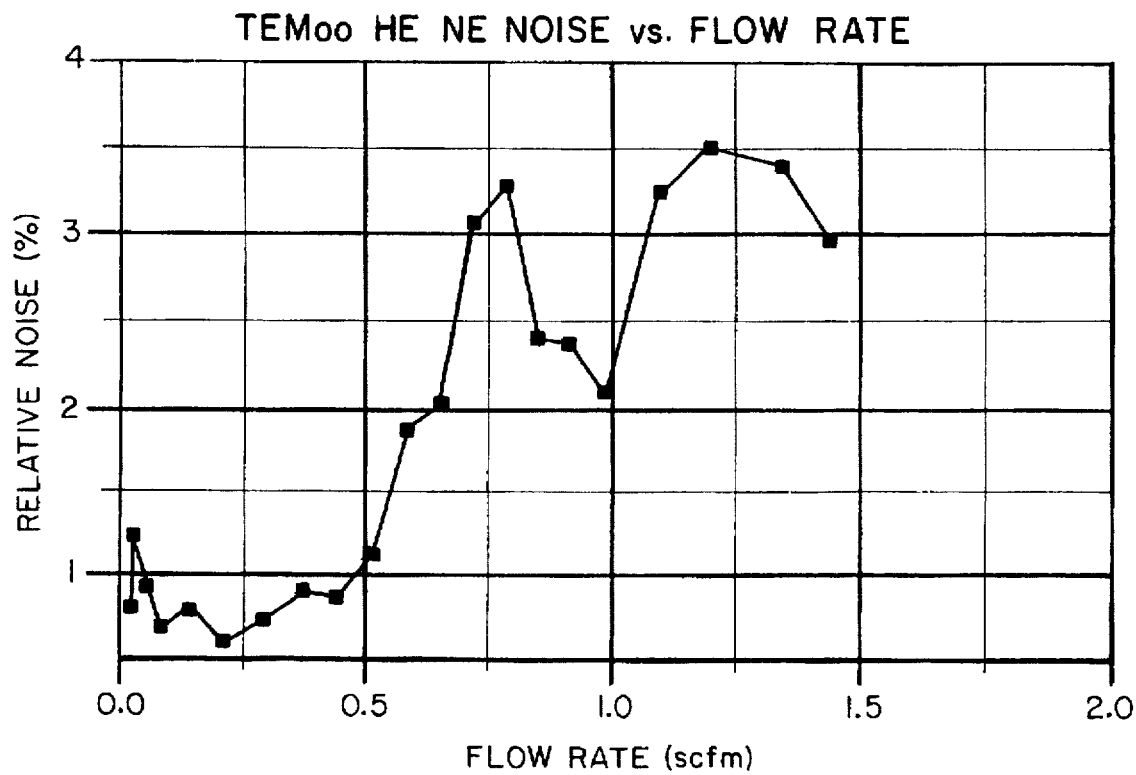
*Fig_2B*

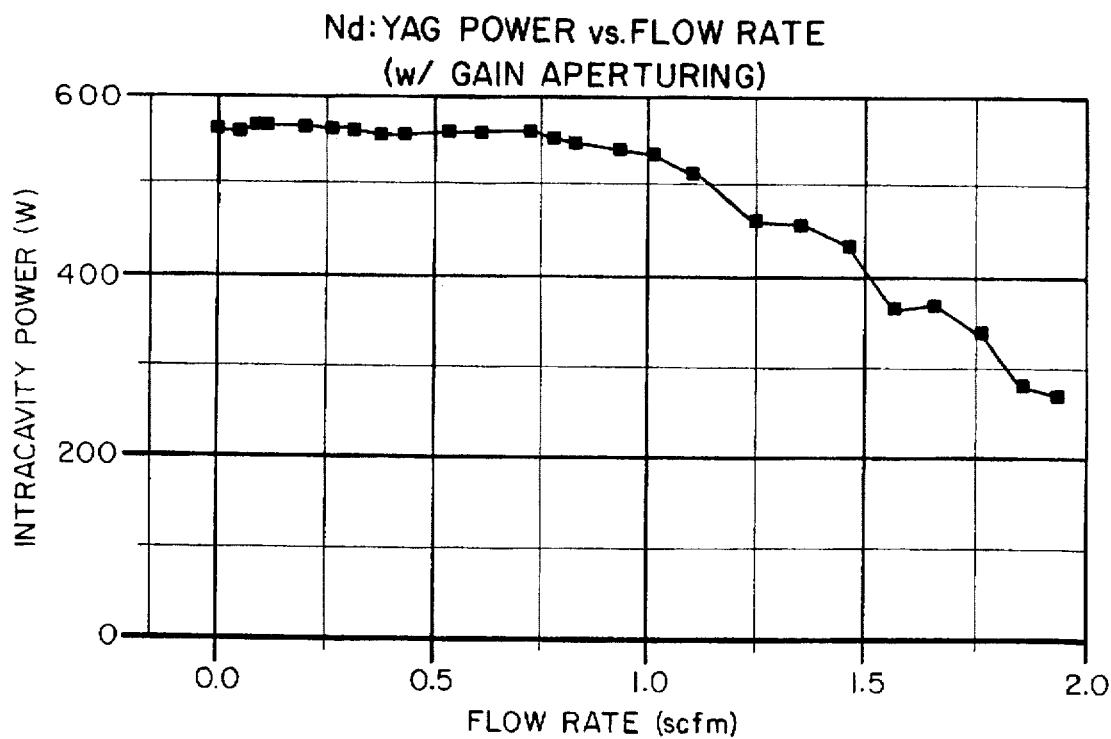
Fig_4A
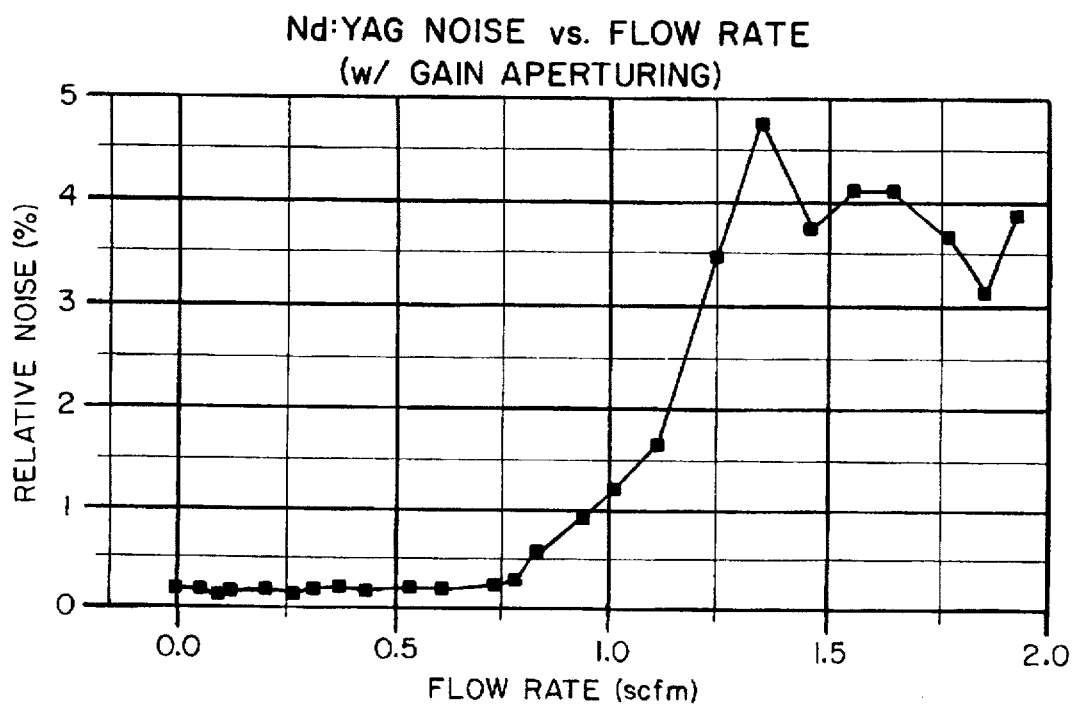
Fig_4B

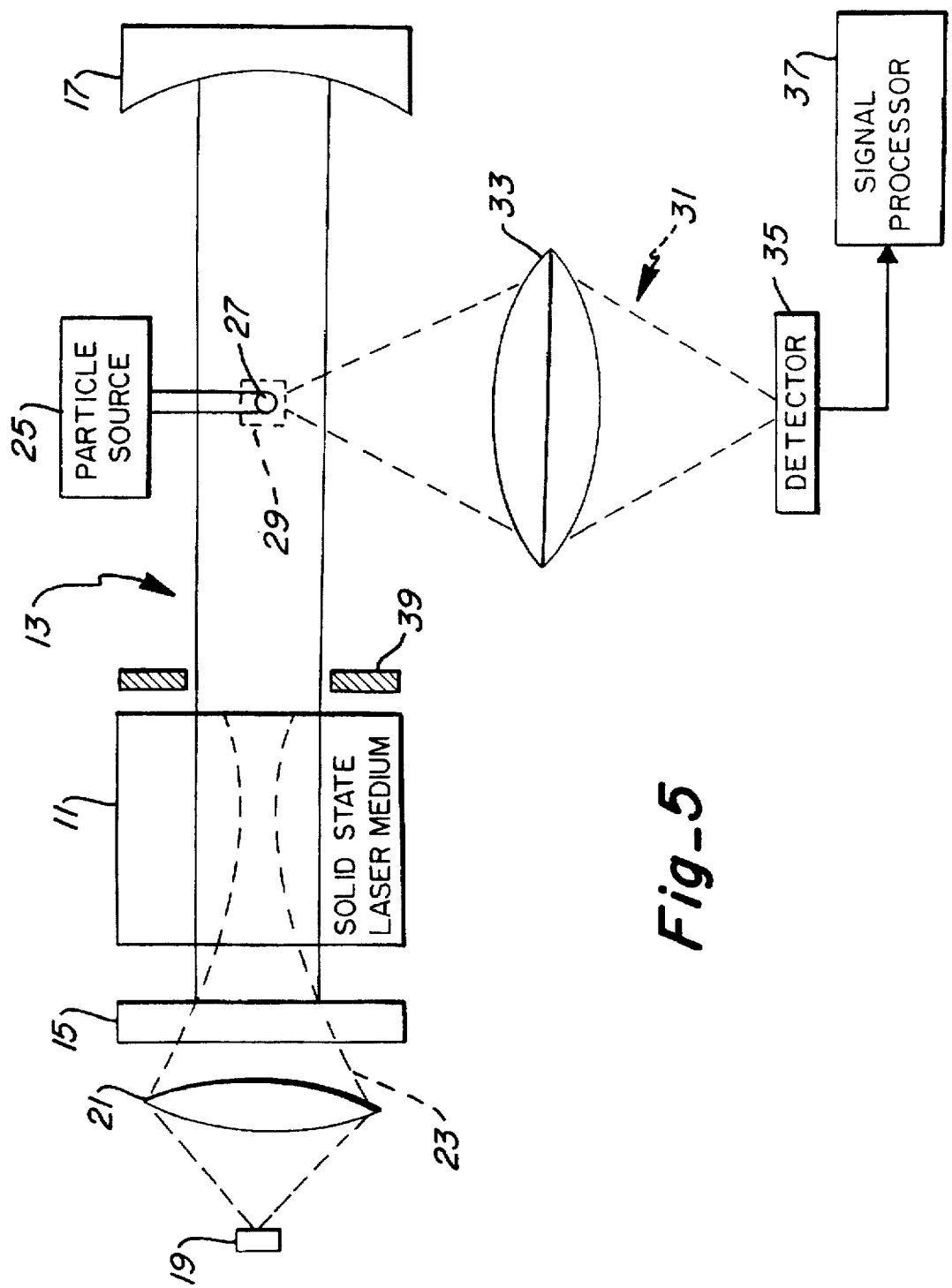
Fig_5

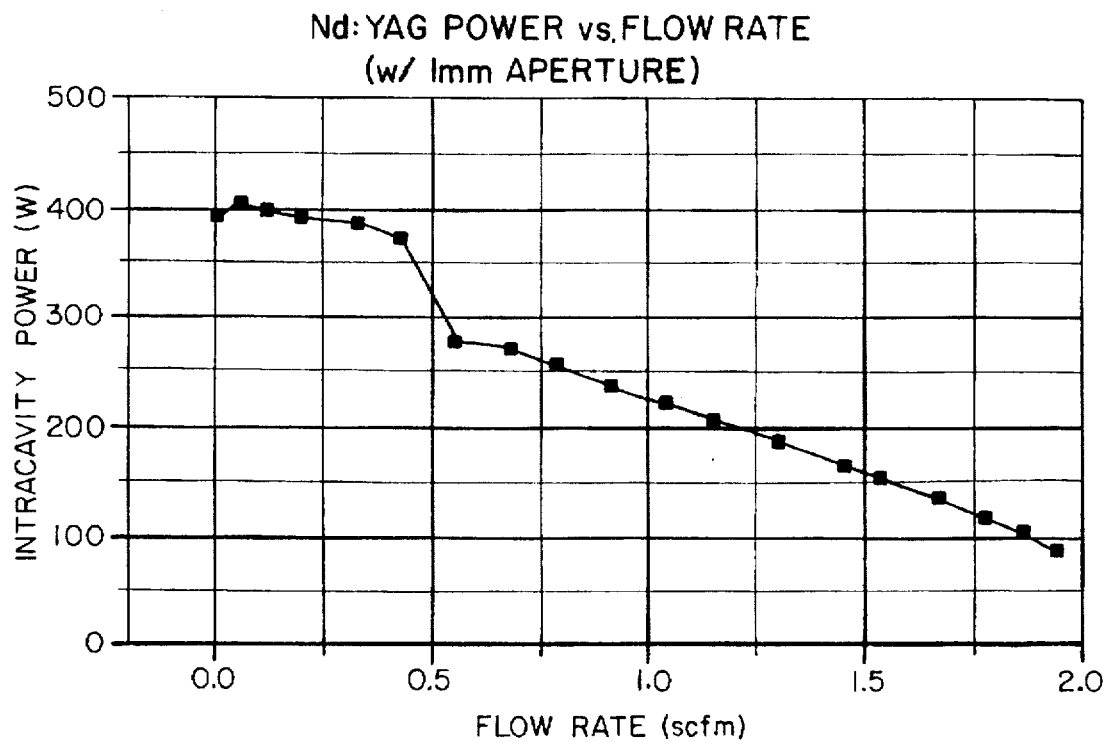
Fig_6A
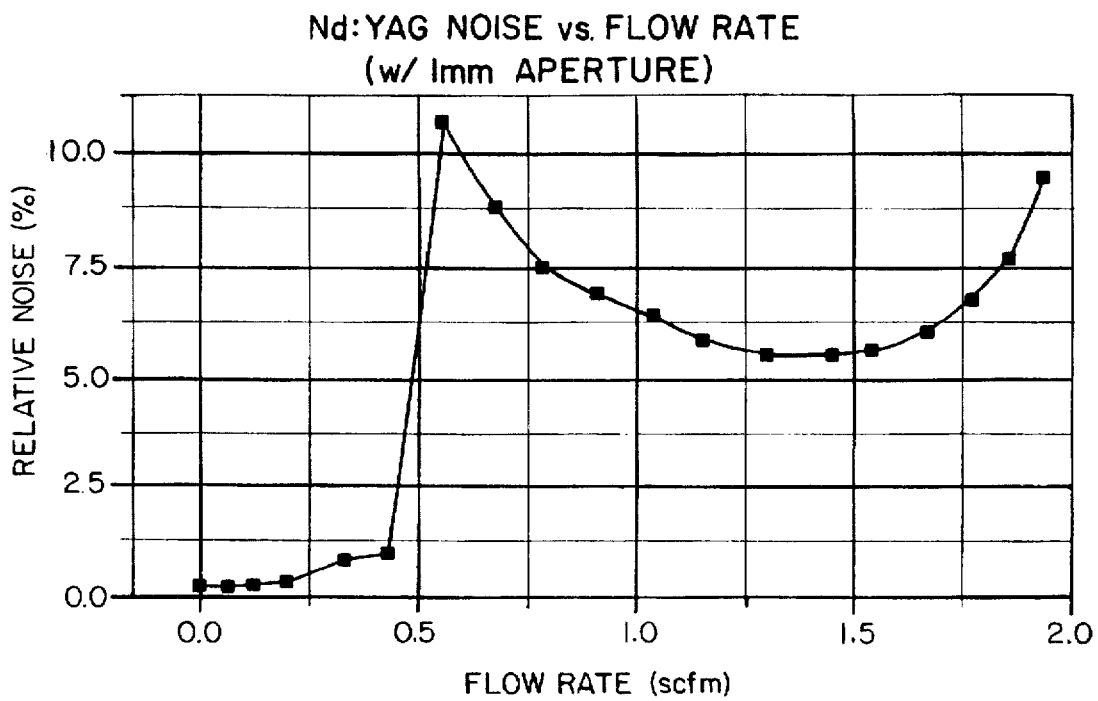
Fig_6B

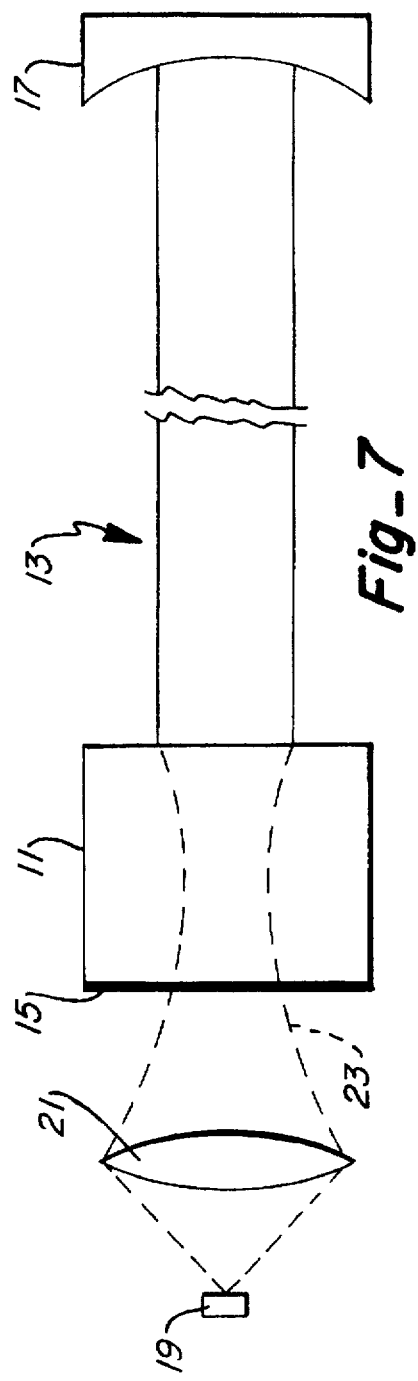
Fig_7
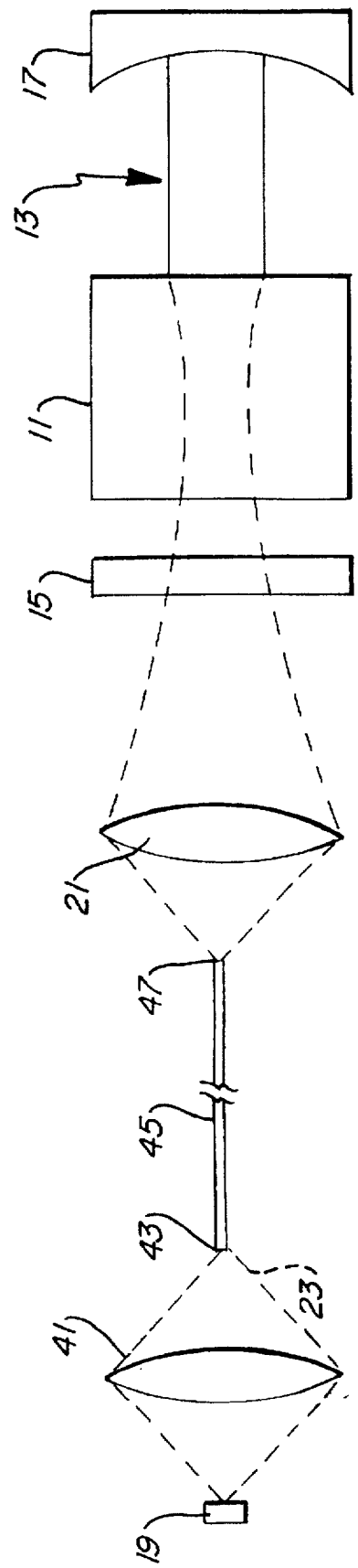
Fig_8

INTRACAVITY PARTICLE DETECTION USING OPTICALLY PUMPED LASER MEDIA

FIELD OF THE INVENTION

This invention relates to particle detection, and, more particularly, relates to intracavity particle detection using optically pumped laser media.

BACKGROUND OF THE INVENTION

The use of detection devices for detection of particles in fluid is now well known, and such devices have been increasingly capable of detecting particles of ever smaller size, including detection of particles in fluids moved at ever increasing flow rates.

Scattering of laser light is now the most commonly used technique for the detection of small submicron airborne particles that are often deleterious to critical manufacturing processes. In this technique, a jet of particle-containing sample air is directed to intersect a laser beam at a detecting region so that particles entrained in the sample air scatter light at the detecting region. The scattered light is thorn collected and detected with the size of the small particles being usually inferred from the size of the scattered light signals.

The utility of a light scattering device for monitoring of small particles is primarily a function of the sensitivity of the device (i.e., the minimum particle size detectable) and the flow rate at which sample fluid, such as air, can be monitored. Often times, these present conflicting requirements since sensitivity normally decreases as the flow rate increases.

To maximize the sensitivity of a device, it is common to place the scattered light detecting region inside the active (or passive) optical laser cavity. By so doing, advantage can be taken of the high circulating laser light intensity that can be generated inside low loss optical resonators without resorting to the costs and hazards normally associated with high output power lasers.

To achieve a high sampling rate, high flow rates are normally required through a limited volume detecting region (jet velocities on the order of 10 meters per second being common). Such high flow rates introduce both static and time varying gradients in the index of refraction in the scattering region which perturb the laser cavity, and these perturbations may modify the transverse mode structure of the laser cavity and degrade the amplitude stability of the intracavity laser power. Ultimately, the maximum sample flow rates of devices of this type are limited, and much of the technical content of current instrumentation is concerned with management of sample flow induced measurement noise.

Most now known commercial intracavity light scattering devices employ gas lasers, with the Helium Neon (HeNe) laser having been found to be particularly useful since it can be manufactured with very low cavity losses (on the order of 100 parts per million) and because of its low cost and long useful life. Particle detection using HeNe lasers is shown, for example, in U.S. Pat. Nos. 4,571,079, 4,594,715 and 4,798,465, and is also discussed in an article by R. G. Knollenberg entitled "The Measurement of Particle Sizes Below 0.1 Micrometers", Journal of Environmental Science, January–February 1985.

Using gas lasers, it is now possible to achieve intracavity powers on the order of about 50 Watts from a plasma tube approximately 300 millimeters in length, with the most common methods for excitation of gaseous laser media employing electrical discharges (commercial HeNe lasers, for example, commonly use a DC glow discharge with a discharge current on the order of 5 milliamperes).

With this type of excitation, it is necssary to employ a physical structure (usually a glass capillary tube) to confine the electrical discharge to a region of space small enough for effective overlap with the laser mode so that efficient laser operation is realized. The physical structure that confines the discharge, however, will also partially occlude the laser modes and introduce optical losses that depend on the transverse mode number of the mode (this is commonly referred to as diffraction loss and is usually employed to control the transverse mode structure of a gas laser).

The presence of physical aperturing of the laser modes found in gas lasers has been found to be a significant drawback in high flow rate intracavity light scattering applications. Sample flow induced index of refraction gradients cause deviations of the beam path within the laser cavity and therefore shift the beam position with respect to the cavity aperture (or apertures) and/or distort its shape. Thus, the sample flow modulates the diffraction loss of the laser cavity. This manifests itself as a static or time varying reduction in intracavity power, or modification of the transverse mode structure of the laser, and typically degrades the signal-to-noise ratio of light scattering devices.

In general, there is also a time varying component to the flow perturbation due to the presence of turbulence in flow jets. These time varying perturbations can significantly increase the noise level of the intracavity power and degrade the sensitivity of the light scattering device.

The effect of sample flow in gas laser cavities is so severe that fundamental mode HeNe cavities are typically extinguished by flow rates on the order of one cubic foot per minute (1 CFM) that are common in now known commercial devices. It has been found that higher order transverse mode cavities (with transverse mode numbers of approximately 3 to 5) are less perturbed by sample flow and are now preferred for high flow rate applications. The use of multimode cavities, however, usually requires more sophisticated noise cancellation techniques to separate the signal from small particles from that of the background from molecular scattering.

A simplified side section schematic presentation of a now known particle detection device using a HeNe plasma tube and having laser light intersected at a detecting region by a particle-containing air stream is shown in FIG. 1. In the particle detecting device shown in FIG. 1, about 12 Watts of intracavity power can be achieved in a $TEM_{oo}$ transverse mode under zero flow conditions.

The effect of sample flow in the prior art device, as shown in FIG. 1, is illustrated in FIGS. 2A and 3B. The degradation of intracavity power due to increasing flow rates is readily apparent in FIG. 2A with the intracavity power reaching negligible values for flow rates not much greater than 0.1 SCFM (standard cubic feet per minute) and far less than 1 SCFM, and dramatic increases in the relative noise due to increasing flow rates are readily apparent in FIG. 2B even at flow rates well below 1 SCFM.

The use of an optically pumped, solid state laser medium, and, more particularly, a solid state laser medium, such as, for example, a Neodymium doped (1.1% by weight) Yttrium Aluminum Garnate (Nd:YAG) crystal, end-pumped by one or more laser diodes is shown, for example, in U.S. Pat. Nos. RE 34,729, 4,653,056, 4,723,257 4,739,507, 4,809,291 and 4,872,177, with U.S. Pat. No. 4,723,257 also showing optical coupling of light to the solid state laser medium, and it is suggested that a diode pumped solid state laser medium could include Nd:YVO$_4$, Nd:YLF, Nd:YAP, Nd:YALO, Nd:glass, Nd:BEL, and Nd:GSGG, as well as Nd:YAG. None of these patents, however, appear to be directed to particle detection or particle detection using an optically pumped solid state laser medium in a laser cavity in conjunction with a detecting region also within the laser cavity.

SUMMARY OF THE INVENTION

This invention provides particle detection using optically pumped laser media. A laser medium, such as a solid state laser medium, normally positioned within a laser cavity, is pumped (preferably end-pumped) by an optical pump source, such as a semiconductor laser, to excite the laser medium to provide laser light within the laser cavity. A detecting region, also preferably within the laser cavity, is exposed to the laser light whereby detectable particles, such as small particles (i.e., particles having a size of 0.05 to 10 microns), which particles may be in fluid, within the detecting region affect the light in a predetermined manner, such as by scattering the light, so that the affected, or scattered, light is indicative of the detectable particles.

High intracavity power, greater than 100 Watts and up to 500 Watts and greater, can be achieved in a laser cavity having therein a solid state laser medium, such as a doped medium, including a Neodymium doped medium (a Nd:YAG or a Nd:YVO$_4$ crystal, for example) or a Chromium doped medium (a Cr:LiSAF crystal, for example.), end-pumped by a semiconductor laser, such as a Gallium Aluminum Arsenide (GaAlAs) structure, providing power greater than 100 mW (milliwatts)and up to about 500 mW and focused into the laser medium to achieve gain-aperturing (as defined hereinafter), to scatter light at a detecting region within the laser cavity with small particles being detected while passing through the detecting region at high flow rates, including flow rates at, or greater than, one cubic foot per minute.

It is therefore an object of this invention to provide an improved particle detecting device and method.

It is another object of this invention to provide a novel detection device and method using optical laser media.

It is still another object of this invention to provide a novel particle detecting device and method using a laser medium within a laser cavity end-pumped by an optical pump source.

It is still another object of this invention to provide a novel particle detecting device and method using a solid state laser medium end-pumped by an optical pump source such as a semiconductor laser.

It is still another object of this invention to provide a novel particle detecting device and method using a solid state laser medium end-pumped by an optical pump source with the pumped light from the optical pump source being focused into the laser medium to provide gain-aperturing.

It is still another object of this invention to provide a novel particle detecting device and method using a laser medium excited by an optical pump source to provide laser light and a detecting region having particles therein that cause scattering of light at the detecting region to enable particle detection.

It is another object of this invention to provide a novel particle detecting device and method using a solid state laser medium end-pumped by an optical pump source to provide high intracavity power for detection of particles.

It is another object of this invention to provide a novel particle detecting device and method to enable detection of small particles moved through a detection region at high flow rates, including flow rates at, or greater than, one cubic foot per minute.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIGS. 2A and 2B are graphs illustrating the effect of flow rate of particle-containing fluid through the detecting region of the device, as shown in FIG. 1, for intracavity power (FIG. 2A) and relative noise (FIG. 2B);

FIGS. 4A and 4B are graphs illustrating the effect of flow rate of particle-containing fluid through the detecting region of the device of this invention, as shown in FIG. 3, for intracavity power (FIG. 4A) and relative noise (FIG. 4B;

FIG. 5 is a schematic side section presentation illustrating a particle detecting device as shown in FIG. 3 except using physical aperturing;

FIGS. 6A and 6B are graphs illustrating the effect of flow rate of particle-containing fluid through the detecting region of the device, as shown in FIG. 5, for intracavity power (FIG. 6A) and relative noise (FIG. 6B);

FIG. 7 is a partial schematic side section presentation like that of FIG. 3 but illustrating use of a coating on the laser medium to form a mirror; and FIG. 8 is a partial schematic side section presentation like that of FIG. 3 but illustrating optical coupling of light using a fiber optic coupler from the optical pump source to the laser medium.

DESCRIPTION OF THE INVENTION

In this invention, a fundamentally different type of laser media and pumping mechanism is utilized for detection of particles, and particularly detection of small particles (i.e., particles having a size less than 0.1 microns), to provide a significant reduction in flow related performance degradation in intracavity light scattering devices. As used herein, optically pumped laser media, and particularly, solid state laser media, provide significant performance advantages over now known detecting devices, including greater resistance to flow induced perturbations.

Figure 3:
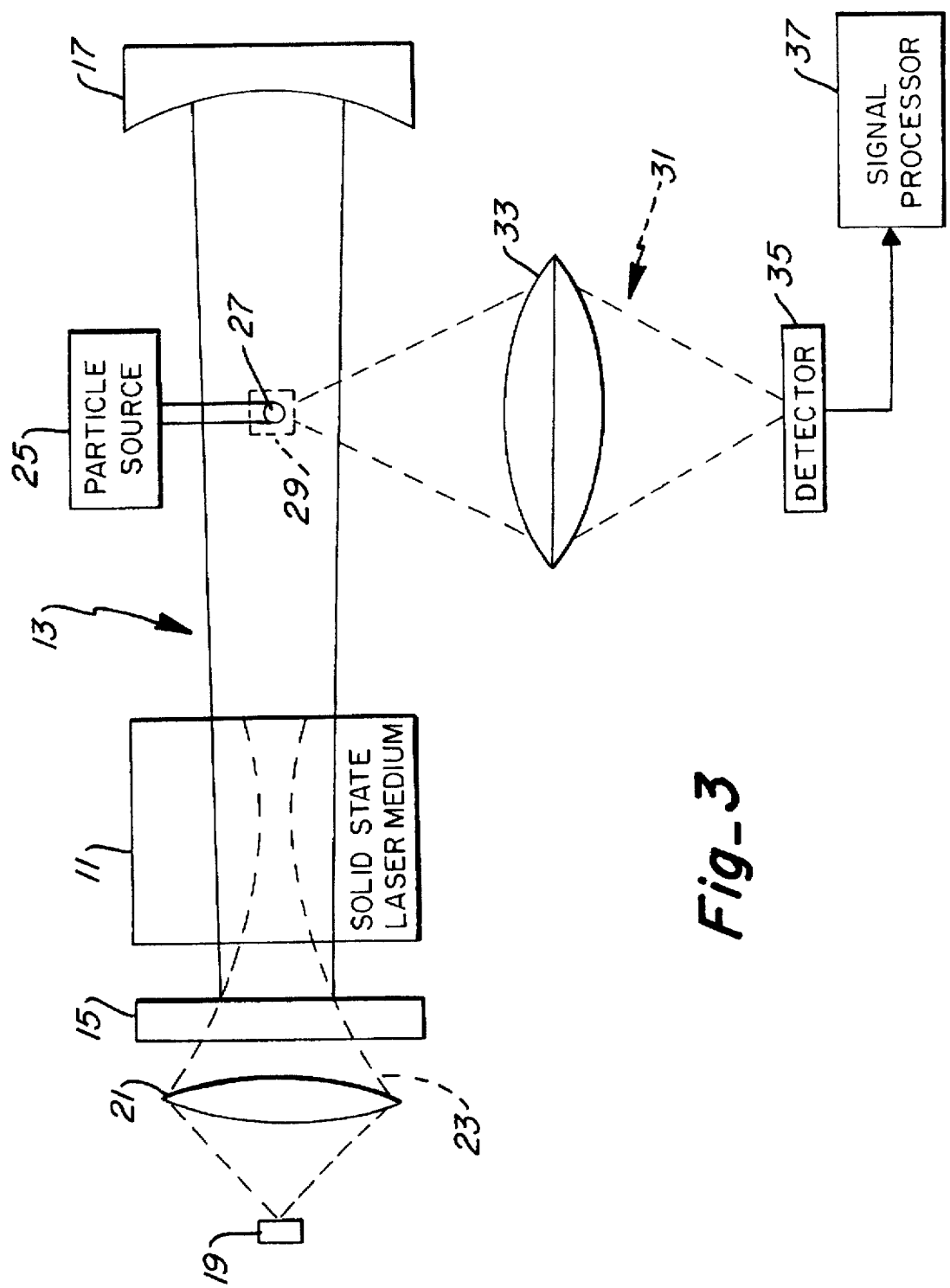
FIG. 3 is a schematic side section presentation illustrating the particle detecting device of this invention.

As indicated in FIG. 3, laser medium 11 is preferably a solid state laser medium, such as a doped medium, including a Neodymium doped medium (a Nd:YAG or a Nd: YVO$_4$ crystal, for example, with other such Nd:doped media, such as Nd:YLF, Nd:YAP, Nd:YALO, Nd:glass, Nd:BEL, and Nd:GSGG being also suggested for use) or a Chromium doped medium (a Cr:LiSAF crystal, for example). At present, a Neodymium doped (1.1% by weight) Yttrium Aluminum Garnate (Nd:YAG) crystal is preferred, with a Neodymium doped Yttrium Vanadate Oxygen (Nd:YVO$_4$) crystal or a Chromium doped Lithium Strontium Aluminum Fluoride (Cr:LiSAF) crystal being now next preferred.

As also indicated in FIG. 3, laser medium 11 has a 5 mm (millimeter) transverse path length and is positioned within laser cavity 13 adjacent to a first mirror 15. Mirror 15 is indicated in FIG. 3 to be a planar mirror and is positioned at one, or a first, end of laser cavity 13, and a second mirror 17 is indicated in FIG. 3 to be a concave mirror, having a radius of 20 cm (centimeters), with second mirror 17 being positioned at the opposite, or second, end of the laser cavity, with the mirrors being spaced 12 cm so that the transverse length of laser cavity 13 is 12 cm. Mirrors 15 and 17 could be other than as specifically indicated in FIG. 3, including, for example, both being planar or concave mirrors or oppositely positioned to that shown in FIG. 3.

As further indicated in FIG. 3, laser medium 11 is end-pumped by optical pump source 19 providing a light output that is collected and focused by focusing unit 21 to provide pump beam 23 through a first mirror 15 into laser medium 11. In addition, particles from particle source 25 (which may be, for example, a particle-containing fluid, such as air, source) are injected through sample jet 27 so that the particles are passed through laser cavity 13 between laser medium 11 and a second mirror 17, as indicated in FIG. 3, so that the particles pass through detecting region 29 to intersect the laser light, or beam, from laser medium 11 thereat.

A conventional collection, detection and processor unit 31 is utilized to view the detecting region in order to collect and detect light affected, or scattered, by particles at the detecting region. Unit 31 is usually positioned normal to both the laser beam from the laser medium and the sample flow such that unit 31 views the intersection of the laser beam and the sample flow. As indicated in FIG. 3, unit 31 normally includes a focusing lens 33, a detector (usually a photodetector or photodetector array) 35, and a signal processor 37. Unit 31 can, for example, be a unit as shown in U.S. Pat. No. 4,571,079, or a unit as shown in U.S. Pat. No. 4,798,465 to achieve greater sensitivity.

Optical pump source 19 is preferably a single broad area emitter Gallium Aluminum Arsenide (GaAlAs) semiconductor laser with an emission wavelength of about 808 nm. The focused light from focusing unit 21 preferably has a transverse extent of less than 250 microns over a 5 mm path length. Mirrors 15 and 17 have greater than 99.99% reflectance at 1,064 nm (the wavelength of the fundamental transverse mode of the laser cavity), and mirror 15 is coated to provide high (greater than 90%) transmission, or being highly transmittive, at the pump wavelength (808 nm).

When a solid state laser medium is optically pumped by a source with sufficiently high spatial brightness, it is not necessary to use physical apertures in the laser cavity to control the transverse mode structure of the laser. Instead, the pump light can be focused into the laser medium such that the pumped volume lies substantially within the fundamental transverse mode of the laser cavity. Under these conditions, the fundamental mode is most effective in extracting optical energy from the pumped volume and the laser oscillates only in the fundamental mode. This is referred to as gain-aperturing and is most easily achieved with coherent, or semi-coherent, sources of pump light, of which semiconductor lasers are an important practical example.

With the device as shown in FIG. 3, the transverse extent of the pumped volume is less than 250 microns, while the laser mode has a minimum diameter of 360 microns. Thus, this arrangement clearly satisfies the condition of having the pumped volume lie substantially within the laser mode volume, and hence gain-aperturing is clearly achieved.

An important feature of a gain-apertured laser cavity is that its performance characteristics are only weakly dependent on the details of the shape, size or alignment of the pumped volume with respect to the laser cavity mode, as long as the pumped volume remains substantially within the laser mode volume. Therefore, the device of this invention, as shown in FIG. 3, is quite tolerant of relative misalignments between the laser cavity mode and the optical pumping beam.

Significant performance advantages over prior devices are realized using the foregoing. Flow induced beam deviations within the laser cavity affect much more weakly the characteristics of the intracavity beam. In addition, the flow has essentially no effect on the cavity losses due to the absence of physical apertures in the cavity and, due to the nature of the gain-apertured laser cavity, it has only a weak effect on the gain.

Thus, a particle detection device having a gain-apertured solid state cavity is more resistant to flow induced perturbations than now known particle detection devices. This is particularly relevant where a particle-containing fluid flow across the laser light perturbs the cavity by causing a deviation of the laser mode axis since the presence of a physical aperture under these conditions will normally cause increased cavity losses (with an unperturbed cavity and proper focusing of the pump light so that the pumped volume lies substantially within the fundamental transverse mode of the laser cavity, TEM$_{oo}$ operation is realized with any physical aperture in the system being so large that diffraction loss is negligible, while with no physical apertures, cavity losses are essentially unchanged by such deviations). In addition, if the deviation is of modest size, the pumped volume will still lie substantially within the laser mode and TEM$_{oo}$ operation will be maintained, with little change in the gain and, therefore, the intracavity power.

With the optical arrangement as shown in the device of FIG. 3, about 550 Watts of intracavity power has been observed in a working embodiment of the invention in a TEM$_{oo}$ transverse mode at 1,064 nm with an incident pump power of about 500 mW (milliwatts).

Figure 1:
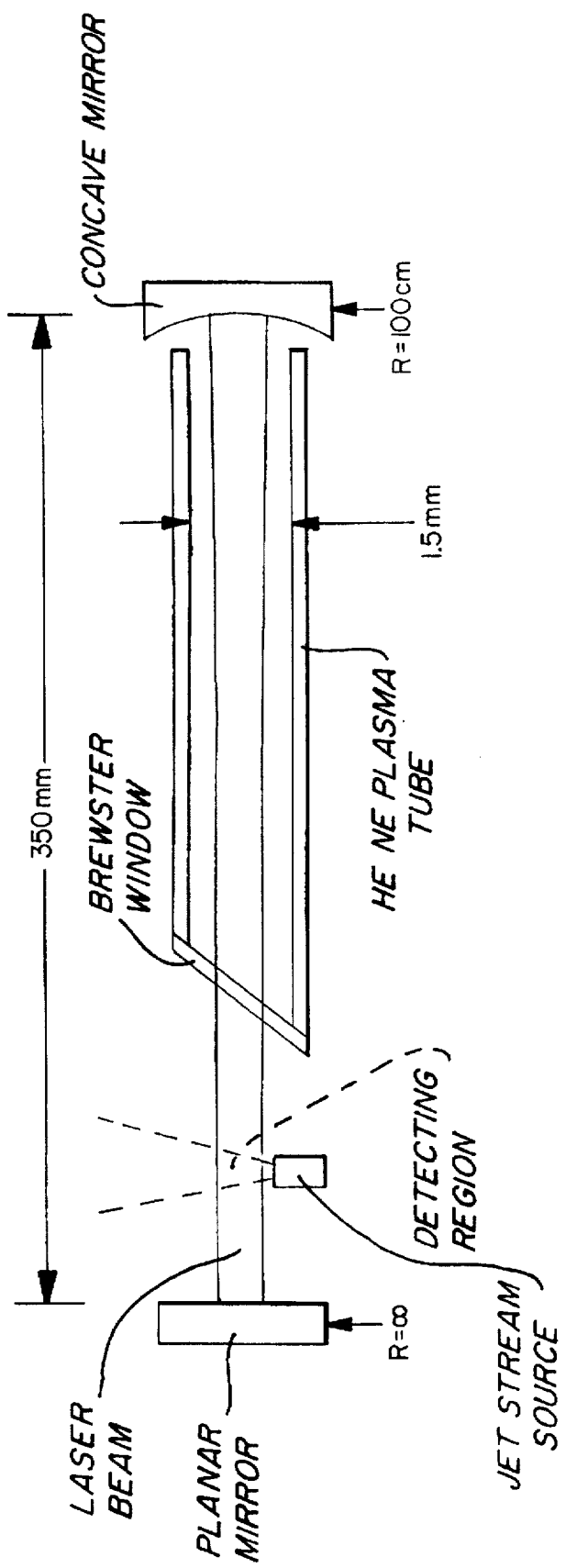
FIG. 1 is a schematic side section presentation illustrating a now known particle detecting device having a HeNe laser.

The effect of the sample flow on the particle device of this invention as shown in FIG. 3 is shown by the graphs of FIGS. 4A and 4B. From these graphs it is clearly apparent that the device of this invention is far less susceptible to degradation by large, or high, flow rates than prior art devices such as shown in FIG. 1 in conjunction with the graphs of FIGS. 2A and 2B. Sample flow rates greater than 1 SCFM can be achieved, and this represents an approximate order-of-magnitude improvement over prior art devices with a TEM$_{oo}$ mode structure being maintained over the entire range of sample flow rates presented in the graphs of FIGS. 4A and 4B.

To show the importance of physical apertures with respect to sample flow induced perturbations, a device similar to that shown in FIG. 3 is illustrated in FIG. 5, except the device, as illustrated in FIG. 5, has a physical aperture 39 (a thin metallic aperture, such as 1.0 mm in diameter) added within the laser cavity to add a non-trivial level of diffraction loss (the cavity power was reduced by about 30%, this being an amount comparable to the loss necessary to enforce TEM$_{oo}$ operation in a gas laser device. As shown by the graphs of FIGS. 6A and 6B, the presence of the physical aperture adversely effects intracavity power and relative noise as flow rate is increased. It is to be noted, however, that the physically apertured device, as shown in FIG. 5, still has a significant improvement in resistance to sample flow induced degradation (as shown by the graphs of FIGS. 6A and 6B) than does the prior art device, as shown by FIG. 1 in conjunction with the graphs of FIGS. 2A and 2B.

As indicated in FIG. 7, mirror 15 can be formed as a coating on the outside wall of solid state laser medium 11, as is now preferred for at least some devices. The light from optical pump source 19 and focused through lens 21 is coupled through the coating forming mirror 15 into laser medium 11 in the same manner as brought out above where mirror 15 is adjacent to, but separated from, laser medium 11, as shown in FIG. 3, and laser light from laser medium 11 is scattered by particles at detecting region 29 within the laser cavity in the same manner as described above in connection with FIG. 3. When mirror 15 is formed as a coating on laser medium 11, the mirror acts in the same manner as described above with respect to mirror 15, as shown in FIG. 3, to reflect light within resonant cavity 13 at the fundamental mode of the resonant cavity.

The light from optical pump source 19 may also be coupled from the optical pump source to lens 21 and laser medium 11 using optical coupling that includes fiber optics. As indicated in FIG. 8, lens 41 may be used to receive light from optical pump source 19 so that lens 41 focuses the light into the input end 43 of fiber optic coupler 45, with light from the output end 42 of coupler 45 being received at lens 21 in the same manner as described above with respect to FIG. 3, and, again, laser light from laser medium 11 is scattered at detecting region 29 within the resonant cavity in the same manner as described in connection with FIG. 3.

An added advantage of this invention is that optically pumped solid state laser media typically have much higher gain coefficients and smaller pump volumes than gas laser media. Thus, efficient operation can be realized with smaller laser mode sizes that are typical of shorter cavity spacings and shorter radius of curvature mirrors than with known gas laser systems. It is well established that laser cavities with short radius mirrors are less susceptible to perturbations than those with long radius mirrors.

From the foregoing, it is to be realized that this invention provides a novel device and method for intracavity detection of particles using optically pumped laser media.

What is claimed is:

1. A device for intracavity detection of particles, said device comprising:
    a laser cavity;
    a solid state laser medium for providing laser light in said laser cavity when excited;
    an optical pump source for providing pumping light;
    a focusing unit for focusing said pumping light provided by said optical pump source into said solid stat laser medium to achieve gain-aperturing of said laser cavity and to excite said solid state state laser medium to provide intracavity power greater than 100 W within said laser cavity; and
    detecting region having particles therein, said detecting region being within said laser cavity and in the path of said laser light so that light in said detecting region is affected by at least detectable portion of the particles in said detecting region such that said affected light is indicative of said detectable portion of said particles.

2. The device of claim 1 wherein said solid state laser medium is within said laser cavity.

3. The device of claim 1 wherein said solid state laser medium is one of a Neodymium and a Chromium doped medium.

4. The device of claim 1 wherein said solid state laser medium is one of a Nd:YAG, a Nd:YVO$_4$ and a Cr:LiSAF crystal.

5. The device of claim 1 wherein said laser medium is end-pumped by light from said optical pump source.

6. The device of claim 5 wherein said device includes optical coupling for coupling said light from said optical pump source to said laser medium.

7. The device of claim 6 wherein said optical coupling includes a fiber optic coupler.

8. The device of claim 5 wherein said optical pump source is a semiconductor laser.

9. The device of claim 8 wherein said semiconductor laser is a GaAlAs structure.

10. The device of claim 1 wherein said laser cavity operates in the fundamental transverse mode.

11. The device of claim 10 wherein said laser cavity includes first and second mirrors with both said mirrors being highly reflective at the wavelength of the fundamental transverse mode of said laser cavity, and said first mirror being highly transmittive at the wavelength of said light from said optical pump source.

12. The device of claim 11 wherein said first mirror is formed as a coating on said laser medium.

13. The device of claim 1 wherein said optical pump source provides light to said laser medium at a wavelength of about 808 nm to cause excitation of said laser medium at a fundamental mode wavelength of about 1.064 nm.

14. The device of claim 1 wherein said detecting region is connected with a particle supply source.

15. The device of claim 14 wherein said particles supplied from said particle supply source are moved through said detecting region at a predetermined rate.

16. The device of claim 15 wherein said particles are within a fluid moved through said detecting region at a flow rate over 0.1 CFM.

17. The device of claim 1 wherein said light is scattered by said detectable portion of said particles.

18. The device of claim 18 wherein said device includes a collector unit for receiving scattered light from said detecting region, said collector providing an output indicative of light scattered by said detectable portion of said particles.

19. A device for intracavity detection of particles, said device comprising:
    a laser cavity having a transverse path length;
    a solid state laser medium within said laser cavity, said solid state laser medium having a transverse path length with said transverse path length of said laser cavity being greater than twice said transverse path length of said solid state laser medium;
    an optical pump source for end-pumping said laser cavity to excite said solid state laser medium to provide a beam of laser light in said laser cavity; and
    a detecting region connected to pass particles through said detecting region, said detecting region being within said laser cavity and spaced from said solid state laser medium, and said detecting region also being in the path of said beam of laser light whereby light is scattered by particles in said detecting region with said scattered light being detectable and indicative of particles causing said light to be scattered.

20. The device of claim 19 wherein said device includes a focusing unit to focus light from said optical pump source into said solid state laser medium.

21. The device of claim 20 wherein light is focused into said solid state laser medium to achieve gain-aperturing of said laser cavity.

22. The device of claim 19 wherein said laser cavity has a first mirror through which said solid state laser medium is end-pumped by said optical pump source, a second mirror defining the length of said laser cavity in conjunction with said first mirror, and wherein said solid state laser medium is positioned adjacent to said first mirror.

23. The device of claim 19 wherein said laser cavity provides greater than 100 W of intracavity power in the fundamental transverse mode.

24. The device of claim 19 wherein said particles are within a fluid are moved through said detecting region at a flow rate over 0.1 CFM.

25. A device for intracavity detection of particles, said device comprising:
    a laser cavity having first and second ends and having a first mirror at said first end and a second mirror at said second end with both said mirrors being highly reflective at the wavelength of a predetermined transverse mode of said laser cavity and said first mirror being highly transmittive at a pumping wavelength different from that of said predetermined transverse mode wavelength;
    a solid state laser medium within said laser cavity;
    a semiconductor laser pump source providing laser light at said pumping wavelength;
    a focusing unit for focusing said laser light from said pump source through said first mirror into said solid state laser medium to end-pump said laser medium and thereby excile said solid state laser medium to provide laser light within said laser cavity at said wavelength of said predetermined transverse mode of said laser cavity whereby intracavity power greater than 100 W is produced, said light focused into said solid state laser medium having a volume that lies within said predetermined transverse mode of said laser cavity to thereby achieve gain-aperturing of said laser cavity;
    a fluid path having a detecting region within said laser cavity between said solid state laser medium and said second mirror, said fluid path being provided from a particle-containing fluid source whereby particle-containing fluid is movable through said detecting region at a predetermined flow rate, and said detecting region when exposed to said laser light in said laser cavity causes light to be scattered by particles in said particle-containing fluid moved through said detecting region; and
    a collector for collecting said scattered light from said detecting region, said collected scattered light being indicative of particles causing said light to be scattered.

26. The device of claim 25 wherein said first mirror is formed as a coating on said solid state laser medium.

27. The device of claim 25 wherein said solid state laser medium is one of a Nd:YAG, a Nd:YVO$_4$, and a Cr:LiSAF crystal.

28. The device of claim 25 wherein said focusing unit includes a fiber optic coupler and at least one lens for focusing said light from said pump source through said first mirror into said laser medium.

29. The device of claim 25 wherein said predetermined flow rate of fluid through said detecting region includes a flow rate over 0.1 CFM.

30. The device of claim 25 wherein said device provides at least 500 W of intracavity power with a pumping power of 500 mW.

31. A method for intracavity detection of particles, said method comprising:
    providing a solid state laser medium within a laser cavity;
    providing an optical pump source to provide pumping light;
    focusing said pumping light from said optical pump source into said solid state laser medium to achieve gain-aperturing of said laser cavity and to excite said solid state laser medium to provide laser light within said laser cavity having intracavity power greater than 100 W;
    providing particles at a detecting region within said laser cavity; and
    exposing said detecting region to said laser light within said laser cavity so that particles at said detecting region cause light to be scattered with said scattered light being indicative of said particles.

32. The method of claim 31 wherein said method includes collecting scattered light from said detecting region, and, responsive, thereto, providing an output indicative of said particles causing said light scattering at said detecting region.

33. The method of claim 31 wherein said method includes operating said laser cavity in the fundamental transverse mode.

34. The method of claim 31 wherein said method includes optically pumping said laser medium through a fiber optic coupler.

35. The method of claim 31 wherein said method includes end-pumping of said laser medium to excite said laser medium.

36. The method of claim 31 wherein said particles are within a fluid moved through said detecting region at a flow rate over 0.1 CFM.

* * * * *